US010028927B2

(12) United States Patent
Davis

(10) Patent No.: US 10,028,927 B2
(45) Date of Patent: Jul. 24, 2018

(54) TOPICAL PHARMACEUTICAL FORMULATION

(71) Applicant: Futura Medical Developments Limited, Surrey (GB)

(72) Inventor: Adrian Davis, Surrey (GB)

(73) Assignee: FUTURA MEDICAL DEVELOPMENTS LIMITED, Surrey (GB)

( * ) Notice: Subject to any disclaimer, the term of this patent is extended or adjusted under 35 U.S.C. 154(b) by 0 days.

(21) Appl. No.: 15/551,547

(22) PCT Filed: Feb. 22, 2016

(86) PCT No.: PCT/GB2016/050444
§ 371 (c)(1),
(2) Date: Aug. 16, 2017

(87) PCT Pub. No.: WO2016/132159
PCT Pub. Date: Aug. 25, 2016

(65) Prior Publication Data
US 2018/0036269 A1  Feb. 8, 2018

(30) Foreign Application Priority Data

Feb. 20, 2015 (GB) .................... 1502845.9

(51) Int. Cl.
*A61K 31/196* (2006.01)
*A61K 47/10* (2017.01)
*A61K 9/00* (2006.01)
*A61K 47/14* (2017.01)

(52) U.S. Cl.
CPC .......... *A61K 31/196* (2013.01); *A61K 9/0014* (2013.01); *A61K 47/10* (2013.01); *A61K 47/14* (2013.01)

(58) Field of Classification Search
None
See application file for complete search history.

(56) References Cited

U.S. PATENT DOCUMENTS 8,541,470 B2 * 9/2013 Davis .................. A61K 9/0014
514/567

FOREIGN PATENT DOCUMENTS

| WO | 00/44347 A1 | 8/2000 |
| WO | 2004/017998 A2 | 3/2004 |
| WO | 2005/027977 A2 | 3/2005 |
| WO | 2005/105059 A1 | 11/2005 |
| WO | 2008/110741 A2 | 9/2008 |
| WO | 2011/070318 A2 | 6/2011 |

OTHER PUBLICATIONS

International Search Report issued in corresponding International Patent Application No. PCT/GB2016/050444 dated May 11, 2016.
Written Opinion issued in corresponding International Patent Application No. PCT/GB2016/050444 dated May 11, 2016.

* cited by examiner

*Primary Examiner* — Brian J Davis
(74) *Attorney, Agent, or Firm* — Morgan, Lewis & Bockius LLP

(57) ABSTRACT

Herein described is a topical composition for application of an NSAID, the composition comprising a solution or suspension of the NSAID as active ingredient in a residual carrier system comprising a polyhydric alcohol, a glycol ether, an ester of a higher fatty acid and water, and the ingredients of the residual carrier system have the following concentrations in percentages by weight::polyhydric alcohol 50-90%; glycol ether 7.5-40%; ester 0.5-5%; and water up to 10%. Either the composition or the residual carrier system is a single phase at ambient conditions. The composition may also comprise a volatile solvent such as ethanol or isopropyl alcohol.

33 Claims, 2 Drawing Sheets

TOPICAL PHARMACEUTICAL FORMULATION

FIELD OF THE INVENTION

This invention relates to topical pharmaceutical formulations and, in particular, provides a topical formulation for application of a non-steroidal anti-inflammatory drug (NSAID) for regional transdermal delivery to underlying tissue for analgesic purposes.

BACKGROUND TO THE INVENTION

It is already known to provide formulations containing NSAIDs in the form of gels, creams and sprays intended for topical application for regional delivery to underlying tissues, for the relief of pain and inflammation and to restore mobility. However, some NSAIDs exhibit undesirable side effects either on their own or in interaction with other drugs and, for this reason, there is a continuing need to provide a topical formulation which provides an effective amount for therapeutic activity at the regional tissue target below the application site while at the same time preventing general uptake in the systemic circulation. The objective is to provide local efficacy without the potential for systemic adverse consequences such as gastric, hepatic, renal and other effects. The efficacy of known topical formulations does not compare favourably with that of orally-administered compositions which, however, have general uptake in the systemic circulation.

Many NSAID drugs have been formulated for topical-regional delivery including salicylates, indomethacin, piroxicam, ketoprofen, diclofenac and others. Effective topical therapy, whether for local dermal, regional or transdermal therapeutic purposes, requires the achievement of therapeutic drug concentrations at the target site and depends among other things on drug potency and the extent of skin penetration. For topical regional purposes, diclofenac, ketorolac and ketoprofen are preferred; in particular, the efficacy index for diclofenac (the ratio of its skin penetration to potency) is greater than that for piroxicam by a factor in the order of $10^3$ demonstrating the importance of correct drug selection. Diclofenac and ketoprofen are particularly preferred on the basis of their more rapid systemic clearance compared with other drugs. Overall, diclofenac is generally considered to be the preferred NSAID for topical regional application. Trials of a 1% diclofenac sodium gel for use in treating ostheoarthritis have demonstrated efficacy and safety, although other diclofenac formulations show efficacy which is inferior to that derived from oral therapy. One currently-available formulation is marketed as "Voltarol Emulgel P", containing 1.16% of diclofenac diethyl ammonium, equivalent to 1 g of diclofenac sodium per 100 g of gel.

In terms of achieving optimum benefit to risk ratio following topical application, it is appropriate to consider the rate of individual drug metabolism in the skin (where rapid metabolism would reduce the potential for local efficacy) and clearance from the systemic circulation (where slow clearance would tend to result in therapeutic levels building up in plasma), which factors vary considerably between different drugs. It has been found from in vivo human studies that topical application of a 4% diclofenac sodium gel achieves skin concentrations which are 2-3 times higher than a therapeutic oral dose of 15 mg diclofenac taken 3 times daily for 3 days, despite having a plasma concentration lowered by approximately 60 times.

Certain currently-available formulations of diclofenac salts are based on the use of a non-volatile solvent such as propylene glycol in combination with a volatile solvent such as ethanol or isopropanol or mixtures thereof. The purpose of the volatile solvent is to increase solubility and also to lead to volume reduction on evaporation in use and thus an increase in diclofenac concentration in the non-volatile, residual phase. Supersaturation of the diclofenac salts in the residual phase may occur but, in any event, it is the degree of saturation in the residual phase which drives the percutaneous penetration process, since diffusion is more a function of chemical potential rather than absolute diclofenac concentration. By way of example, the saturated solubility of diclofenac acid in polyethylene glycol is 11.18% w/w, whereas in propylene glycol the saturated solubility is only 1.16% w/w. Despite this, there is no significant difference between diclofenac flux from these respective systems and indeed, because the saturated solubility of the sodium salt of diclofenac acid in propylene glycol is approximately 50% w/w, it is very difficult to achieve saturation, more especially supersaturation, unless either extremely high concentrations of the salt are used, or an extremely low percentage of the residual phase solvent is used. The pH of the formulation may also have an effect on solubility such that lower pH values, for example pH 3.5 to 5.5, decrease solubility of the diclofenac and thus enhance the flux or activity state of the diclofenac in facilitating the achievement of a highly-saturated or supersaturated residual phase.

Attempts to use diclofenac acid in water-ethanol and glycerol-propylene glycol mixtures have been made, based on a concentration of diclofenac acid between 2.5 and 5% by weight of the formulation, it having been calculated that such a dose should deliver an effective but essentially non-systemic regional amount assuming a product application rate of 2.5 $mg/cm^2$/hour. However, since the saturated solubility of diclofenac acid is only 5% w/w even in pure ethanol and also since the saturated solubility in propylene glycol is relatively high, for example compared with glycerol, at around 1% w/w, it is apparent that only low degrees of super-saturation are achievable unless low percentages of propylene glycol are used. Although higher alcohols, for example propanol or iso-propanol, may be used as partial or total replacement for ethanol, it has been found that the respective saturated solubilities for diclofenac acid are in the region of 3-4% and thus are less than in ethanol.

Carrara (US2005/0244522) describes the use of natural (plant derived) skin permeation enhancers in combination with a diethylene glycol ether and, optionally, propylene glycol to deliver a range of drugs including diclofenac diethyl ammonium in cream form. Diclofenac in vitro penetration is approximately twice that of Voltarol gel. Bauer (EP1588697) describes acrylate hydrogels containing an oxyethylene or oxypropylene emulsified lipophilic phase optionally containing propylene glycol and isopropyl myristate to deliver a range of drugs including diclofenac acid and lysine salt in cream form. WO2010/087947 discloses an oily solution of diclofenac in a range of organic solvents and an emollient, for example an oil, a fatty acid or ester, together with antioxidants, surfactants and the like. WO93/00873 describes an aqueous gel for topical application of diclofenac, the gel containing water, low molecular weight alcohols or glycols and ether alcohols and fatty alcohol esters to enhance transdermal flux. US2007/0280972 describes a gel composition including volatile and non-volatile solvents and a gelling agent whereby, on application to the skin, the volatile solvent evaporates and the gelling agent forms a solid gel layer removable by peeling away or washing. Davis (WO 2008/110741) describes a composition for topical application of an NSAID, the composition comprising a solution or suspension of the NSAID as active ingredient in a carrier system comprising a polyhydric alcohol, a glycol ether and an ester of a higher fatty acid, the carrier system being present as a single phase at ambient temperatures and generally including a lower alcohol diluent, water being essentially absent from the carrier system.

In designing topical formulations for enhanced skin penetration of NSAIDS, efforts have hitherto been principally directed at increasing the solubility of the NSAID in the composition as a whole, that is, before application to the skin. However, where the composition contains volatile solvents, the solvents evaporate on application of the composition to the skin and, it is now realised, the flux is dependent not so much on the absolute concentration of the NSAID in the composition as a whole or even in the residual, non-volatile, phase but more on the degree of saturation of the NSAID in the residual phase. In contrast to the goals hitherto pursued, therefore, it is important to employ a residual phase solvent or solvent blend which has a relatively low solvating power for the NSAID, such that the saturated concentration is relatively low and in consequence the concentration of the NSAID in the residual phase is more likely to achieve saturation or even super-saturation as the volatile ingredients evaporate, thus optimising NSAID flux and driving skin penetration. It is also desirable for the NSAID to be lipid-soluble, to enable or enhance penetration of the stratum corneum.

The compositions disclosed in WO2008/110741, referred to above, are essentially anhydrous, it having been thought that the presence of water militated against a single-phase system and, thus, inhibited skin penetration. Water would, it was believed, act (if present) as a volatile solvent, evaporating from the skin on application thereto of the composition and thus having no effect on the composition or penetration properties of the residual phase.

It has now been realised that, contrary to previous understanding concerning the compositions described in WO2008/110741, water forms an equilibrium mixture with the polyhydric alcohol and thus is not subject to total evaporation on application of the composition to the skin. Therefore, instead of acting as a volatile solvent, water is partially retained by the polyhydric alcohol and thus remains as a component of the residual phase. In conjunction with the polyhydric alcohol, water forms a miscible co-solvent reducing the saturated concentration of the NSAID and enhancing its flux in the residual phase. Contrary to the previously-held understanding, therefore, water is of assistance in increasing flux (and, thus, skin penetration) in (and from) the residual phase.

In the compositions described in WO2008/110741, the polyhydric alcohol, preferably a glycol, renders the active ingredient soluble in the stratum corneum barrier and also increases the solubility of the ester. The ester, preferably a polar lipid, has the effect of increasing diffusivity or transport rate through the stratum corneum barrier. However, the polyhydric alcohol and ester are immiscible in the compositions as described and thus do not form a homogeneous, single-phase carrier system for the active ingredient. The glycol ether is included as a co-solvent and has a polarity between that of the polyhydric alcohol and the ester and is present in an amount at least sufficient to solubilise the other two components and provide a homogeneous, single-phase carrier system. The compositions as described contain (based on the residual phase) at least 2% of ester, in order to effectively increase diffusivity through the stratum corneum and thus requiring concentrations, for example from 30-50% or more of glycol ether solvent to achieve solubilisation. However, the glycol ether is also an excellent solvent for diclofenac and thus reduces the degree of saturation of diclofenac in the carrier system. For this reason, and also to allay any concerns relating to skin irritation or allergic dermatitis following repeated or prolonged exposure to such compositions, it may be considered desirable to reduce the concentration of glycol ether solvent.

SUMMARY OF THE INVENTION

In a first aspect, the present invention provides a topical composition for application of an NSAID, the composition comprising a solution or suspension of the NSAID as active ingredient in a residual carrier system comprising a polyhydric alcohol, a glycol ether, an ester of a higher fatty acid and water, the ingredients of the residual carrier system having the following concentrations in percentages by weight:

| polyhydric alcohol | 50-90 |
| glycol ether | 7.5-40 |
| ester | 0.5-5 |
| water | up to 10 | in which either the composition or the residual carrier system is in a single phase under ambient conditions.

Preferred percentage by weight ranges for the ingredients are as follows:

| polyhydric alcohol | 55-80 |
| glycol ether | 15-35 |
| ester | 1-5 |
| water | 2.5-10 |

More preferred percentage by weight ranges for the ingredients are as follows:

| polyhydric alcohol | 50-70 |
| glycol ether | 25-35 |
| ester | 2.5-5 |
| water | 2.5-10 (preferably 5-10) |

Even more preferred percentage by weight ranges for the ingredients are as follows:

| polyhydric alcohol | 60-65 |
| glycol ether | 25-30 |
| ester | 2.5-4 |
| water | 5-10 |

The composition or carrier system being a "single phase" means that the components making up the composition or carrier system form, at equilibrium, a system which is homogeneous thus having uniform physical and chemical characteristics. The components that form the composition or carrier system are all soluble in the percentages at which they are present to form a homogeneous solution.

In contrast, a two phase system has two distinct phases which have distinct physical and/or chemical characteristics (e.g. water and oil) and are separated from each other by a discernible phase boundary.

Preferably, the composition is a single phase at ambient conditions. Preferably, the residual carrier system is a single phase at ambient conditions. In some embodiments, both the composition and the residual carrier system are a single phase at ambient conditions.

The carrier system and/or the composition is single phase at ambient conditions. By "ambient conditions" is meant room temperature under most climatic conditions, say from 5° C. to 40° C., but including the possibility of temperatures down to 0° C. to allow for refrigerator storage. In some embodiments, the composition and/or residual carrier system is single phase at body temperature, for example, about 37° C.

In the compositions according to the invention, as described above, the percentages of the residual carrier system ingredients are relative to the total residual carrier system rather than being relative to the total composition. However, when determining the percentage of each carrier system ingredient and the total residual carrier system (or residual phase), this should be done by analysis of those ingredients within the total formulation "as new", including volatile components, before application in use to the skin. It is to be understood, however, that in use the volatile components will be driven off, thus leaving the residual phase.

In the residual phase, it is possible that there might be less water than in the total formulation as some water might evaporate. However, for the purposes of determining the total residual carrier system and the percentage of water in the residual carrier system so as to assess whether the ingredient percentages fall within the ranges given above, it is the total formulation "as new" which should be analysed.

In reality, the precise amount of water that is retained in the residual phase will depend on the temperature and relative humidity of the ambient atmosphere. If it is desired to analyse the residual phase as such, the total formulation should be subject to conditions under which the volatile components will evaporate, following which, for the avoidance of doubt, the residual phase should be tested at a temperature of 31° C. and relative humidity of 31.9%. The period of time for which the total formulation is left to allow the volatile components to evaporate should not affect the amount of water retained in the residual phase. However, in practice the total formulation should not be left for longer than 30 minutes. Preferably, the total formulation is left for about 20 minutes before testing the water content of the residual phase. The residual phase should contain the same amount of the other components, i.e. the polyhydric alcohol, the glycol ether and the ester, as in the total formulation, although these can also be easily measured by a person skilled in the art. This method can also be used to determine whether the residual carrier system is single phase.

In this specification, the term "volatile", used to qualify the components which evaporate on application of the composition to the skin, means those components which per se have a half-life at a temperature of 32° C. (the normal temperature of human skin) of one hour or less, preferably 30 minutes or less.

In the present invention, the NSAID in the composition may be selected from diclofenac, ketorolac and ketoprofen, preferably as the sole active ingredient. Other NSAIDS which may be used include naproxen and celecoxib. The NSAID may be in salt form or in acid form. In preferred embodiments, the NSAID is diclofenac. The NSAID may be a diclofenac salt, such as the diethylamine salt, or may be diclofenac acid. The NSAID which is preferred for use as the active ingredient in compositions according to the invention is diclofenac due to its cyclo-oxygenase activity in relation to pain and inflammation and because its numerical ratio of skin penetration to potency is superior to most if not all other NSAIDs. The acid form of diclofenac is preferred since it is believed that increased skin penetration results from using diclofenac acid. The acid form is also less soluble than the salt form, whereby it is easier to achieve saturation or super-saturation in the residual phase on evaporation of the volatile components.

The inclusion of water in compositions according to the invention not only forms an equilibrium mixture with the polyhydric alcohol, thus enhancing skin penetration flux or activity state, but also may discourage or prevent esterification of the NSAID by the polyhydric alcohol. NSAIDs which may be esterified include NSAIDs which comprise a carboxylic acid group. Therefore, in some embodiments, the NSAID in the composition is an NSAID which comprises a carboxylic acid group. NSAIDs comprising a carboxylic acid group include diclofenac, ketorolac, ketoprofen and naproxen in their acid forms. Thus, in the present invention, the NSAID may be selected from diclofenac, ketorolac, ketoprofen and naproxen in their acid forms. In preferred embodiments, the NSAID in the composition is diclofenac acid.

Diclofenac acid has a pKa of 4+/−0.2 at 25° C. and it is therefore preferred for the composition to have a pH of 4.0 or lower, to prevent or at least to discourage ionisation and, thus, to enhance its lipid-solubility. However, for improved stability on storage, a pH closer to 7 (neutral) is desirable and accordingly the inclusion of a neutralising agent to increase the pH may be indicated. Suitable neutralising agents include organic amines such as diethylamine, diethanolamine, triethanolamine, lauryl sulphate, tromethamine, diisopropanolamine and ethylenediamine. Suitable inorganic neutralising agents include sodium hydroxide, potassium hydroxide and liquid ammonia. It is desirable for the neutralising agent to be water-miscible and advantageous if it is also volatile, as herein defined, whereby, in use and on application to the skin, the neutralising agent will evaporate together with the other volatile components so that the pH of the remaining (residual) phase will decrease towards the preferred value for optimum skin penetration. Liquid ammonia can be identified as an inorganic neutralising agent which meets this requirement, whereas diethylamine is an example of an organic neutralising agent which may be used. In this way, the composition, before application to the skin and before evaporation of any of the volatile components, may have a pH of 5 to 8, more preferably, 6 to 8, and even more preferably, 6.5 to 7.5. Further, the composition, after application to the skin and after evaporation of the volatile components, may have a pH of 5 or less, more preferably, 4.5 or less, and even more preferably, 4 or less.

The inclusion of water is advantageous as it prevents or discourages esterification of the NSAID, especially in compositions where the pH is less than 5 or more significantly less than 4.5. Put another way, it helps to stabilise the acid form. Water may also act to enhance skin permeability in compositions having a higher pH, around pH 6.5 to 7.5, and may additionally act as a non-solvent to reduce the solubility of the NSAID and, thus, enhance its activity state as the volatile component evaporates. However, water also lowers the solubilising power of the composition for the ester component and reduces its saturated solubility, thereby reducing the maximum amount of ester which can be accommodated without compromising a single phase system, so there is a balance to be struck between too little water for the beneficial properties as set out above and too much water resulting in insufficient ester for efficacy. Thus, the amount of water in the composition should, in any event, be lower than the maximum amount which the composition can contain and yet still remain a single-phase system, either in terms of avoiding precipitation of the NSAID and/or separation of the ester component of the system. The skilled person would readily be able to determine the said maximum amount by trial and error, having regard to the current disclosure. As to the minimum amount of water, the polyhydric alcohol will naturally contain some water. The minimum amount of added water is that which affects the phase boundary of the ester concentration for a given ratio of polyhydric alcohol:glycol ether but for most purposes the minimum water concentration will be 1% based on the residual phase (as hereinbefore defined). In some embodiments, the minimum water concentration may be 2%, or preferably 2.5%, based on the residual phase.

Compositions according to the invention, when applied topically by the fingers to the skin with a rubbing action over an infected or injured target site, form a thin film of from 20-50 microns from which the volatile components evaporate to leave a residual phase which becomes absorbed through the stratum corneum to the underlying tissue. The residual phase continuously releases active ingredients over a period of time to provide a sustained dose to the target site. Compositions according to the invention are preferably in the form of a lotion, cream or gel and include further excipient ingredients as required, including preferably a volatile solvent as diluent.

The polyhydric alcohol is preferably a glycol. The glycol may be selected from glycols having from 3-6 carbon atoms including propylene glycol, dipropylene glycol, 1,5 propanediol butylene glycol, hexylene glycol and glycerol, amongst others. In preferred embodiments, the polyhydric alcohol may be propylene glycol.

The ester of a higher fatty acid may be a polar lipid. The polar lipid, as an exemplary sub-class of the esters of a higher fatty acid, may comprise a branched-chain alkyl ester of a $C_{10}$ to $C_{20}$ saturated carboxylic acid such as isopropyl laurate, isopropyl myristate, isopropyl palmitate or propylene glycol monolaurate. Preferably, the polar lipid comprises a branched-chain alkyl ester of a $C_{10}$ to $C_{16}$ saturated carboxylic acid. Further exemplary esters may include glyceryl stearate and triglycerides such as Miglyol 812 or Labrafil MI944CS. In some embodiments, the polar lipid may comprise a branched-chain alkyl ester of a $C_{12}$ to $C_{20}$ saturated carboxylic acid. In preferred embodiments, the ester may be isopropyl myristate.

The glycol ether, referred to for convenience as a co-solvent with the polyhydric alcohol, is preferably a diethylene glycol ether, for example diethylene glycol monoethyl ether (Transcutol®). Other glycol ethers may include phenoxyethanol, diethylene glycol monomethyl ether and Arlamol PS15.

The amount of the NSAID in compositions according to the invention may be up to 10% by weight. In some embodiments, the NSAID may be present at up to 7.5% by weight. In other embodiments, the NSAID may be present at up to 5% by weight or up to 2.5% by weight. Where the salt of an NSAID is used, the said concentrations relate to the free acid or base. In various embodiments, the NSAID is present at 0.5% to 10% by weight. In a particular embodiment, the NSAID is present at 1% to 10% by weight. In preferred embodiments, the NSAID is present at 0.5% to 6% by weight or at 1% to 5% by weight. The percentages referred to above are with respect to the total formulation.

In preferred embodiments, the composition comprises between 5% and 9% water by weight, between 6% and 8% water by weight, or about 7% water by weight, being expressed as percentages by weight based on the residual carrier system.

The ester preferably ranges from 2.7% to 4.5%, more preferably from 3% to 4%, more preferably still from 3.25% to 3.75%, for example about 3.5%, all concentrations being expressed as percentages by weight based on the residual carrier system.

The glycol ether preferably ranges from 15% to 35%, more preferably from 25% to 30% by weight, for example about 28%, by weight based on the residual carrier system.

The polyhydric alcohol preferably ranges from 55% to 80%, more preferably 60% to 65% by weight, for example about 62%, based by weight on the residual carrier system.

Within the above concentration ranges for the components of the carrier system, the water may be present in a ratio of from 5% to 12.5% of the polyhydric alcohol and the ratio of polyhydric alcohol (including water) to glycol ether is preferably in the range 80:20 to 60:40, more preferably 75:25 to 65:35.

Preferably, compositions according to the invention also include a volatile solvent which, in conjunction with the other components of the carrier system, solubilises the active ingredient at saturation levels and evaporates on application to the skin, thus driving the active ingredient towards or to supersaturation in the residual phase, resulting in enhanced flux of active ingredient. Volatile solvents suitable for use in the present invention includes lower alcohols containing up to 5 carbon atoms, for example ethanol or isopropyl alcohol (IPA), and liquid-phase ketones. In some embodiments, the volatile solvent may be ethanol and/or isopropyl alcohol (IPA). The volatile solvent may be in a range of 15 to 50% by weight relative to the total weight of the composition. In some embodiments, the volatile solvent may be in a range of 15 to 40% by weight relative to the total weight of the composition. Alternatively, the volatile solvent may be in a range of 15 to 30% by weight relative to the total weight of the composition, in a range of 20 to 28% by weight, in a range of 20 to 27% by weight, or in a range of 20 to 26% by weight based on the total composition.

By "liquid phase" in relation to ketones in this specification is meant a ketone having the formula R—C(O)—R which is liquid at ambient temperatures and in which the R groups are the same or different and are alkyl groups optionally substituted by OH, halogen, acetyl (whereby the ketone is acetyl acetone), or other group which, by virtue of its chemical nature or its effect on electron distribution, enhances the solubility properties of the solvent or its rate of evaporation in use. Thus, although higher homologues than acetone, for example, methylethylketone or diethylketone, may be used, acetone is considered to be especially useful because of its ability to undergo keto-enol tautomerism, where the enol form is more stable. Indeed, acetyl acetone, also capable of undergoing keto-enol tautomerism, exists substantially as the enol form.

Optionally, compositions according to the invention contain a polyhydric alcohol including three or more hydroxyl groups as part of the residual carrier system, as a non-solvent to reduce the solubility of the NSAID and, thus, to enhance its activity state. Exemplary polyhydric alcohols for this purpose include glycerol and sorbitol, preferably glycerol, at a concentration up to 15% by weight of the total formulation. In some embodiments, this polyhydric alcohol may be present at up to 12.5% by weight. In other embodiments, the polyhydric alcohol may be present at up to 10% by weight, up to 7.5% by weight, for example, about 5% by weight.

Preferably, the amount of polyhydric alcohol (e.g. glycerol) is 0.5% to 15% by weight of the total composition. In some embodiments, the amount of polyhydric alcohol (e.g. glycerol) is 1% to 15% by weight of the total composition. In other embodiments, the amount of polyhydric alcohol (e.g. glycerol) is 2% to 15% by weight of the total composition. The upper limits described above for the polyhydric alcohol also apply to the ranges. Therefore, for example, the polyhydric alcohol may be present at 1% to 10% or 1% to 7.5% by weight of the total composition. This component, if present, is in addition to the polyhydric alcohol required as an essential ingredient of the carrier system of compositions according to the invention. In order to maintain a single phase, the amount of polyhydric alcohol needs to be adjusted accordingly.

To enhance stability in a supersaturated residual phase which may have a tendency to instability, it is desirable that the composition also includes an antinucleating agent, to discourage recrystallisation of the drug component, which would lead to lower amounts being available for uptake. Nucleation and recrystallisation are likely to be most problematical where higher degrees of supersaturation are experienced in the residual phase. Antinucleating agents may comprise antinucleant polymers, including cellulose, for example hydroxypropyl cellulose, hydroxypropylmethyl cellulose, ethyl cellulose, hydroxypropylmethyl cellulose acetate succinate, and hydroxypropylmethyl cellulose phthalate; pyrrolidones, for example polyvinylpyrrolidone and polyvinylpyrrolidone vinyl acetate copolymer; and acrylates/methacrylates. Such antinucleating agents may be present at between 1% and 5%, between 1% and 3%, or about 2% by weight, based on the total composition.

Compositions according to the invention may also include sensory signals, for example menthol and/or eucalyptus oil. Almost immediately after application these agents give a cooling sensation to the skin which is appreciated by users and heralds the onset of pain relief. Alternatively, the sensory signals may be an agent which gives a warming sensation to the skin after application of the agent.

Other optional ingredients, as known in the art, may be added to compositions according to the invention for formulation purposes depending on the intended mode of application, including thickening or gelling agents such as dimethicone silicone fluid, for example having a viscosity of 0.65CST, propellants for spray formulations and so on. Further optional ingredients may be added to the compositions according to the invention, such as a fragrance.

Rather than specifying the percentages of the carrier system components that form the residual phase in terms of the weight of the carrier system components, the percentages of the components can be specified relative to the total formulation. These percentages relate to the composition as a whole, i.e. before it has been applied to the skin and before any of the volatile components have evaporated.

Therefore, in total formulation terms, compositions according to the invention may comprise, in percentages by weight:

| polyhydric alcohol | 20-60 |
|---|---|
| glycol ether | 5-30 |
| ester | 0.3-3 |
| water | 2.5-10 |
| lower alcohol | 20-50 |

In preferred embodiments, in total formulation terms, compositions according to the invention may comprise, in percentages by weight:

| NSAID | 0.5-5% |
|---|---|
| polyhydric alcohol | 25-50 |
| glycol ether | 10-25 |
| ester | 1-2.5 |
| water | 2.5-10 |
| lower alcohol | 20-50 |

In preferred embodiments, in total formulation terms, compositions according to the invention may comprise, in percentages by weight:

| polyhydric alcohol | 35-50 |
|---|---|
| glycol ether | 17.5-25 |
| ester | 1.75-3.5 |
| water | 3.5-7 |
| lower alcohol | 15-30 |

In addition, the various compositions described above may comprise dimethicone (0.5-2.5% or 1-2%) and/or hydroxypropyl cellulose (1-3% or 1.5-2.5%).

DETAILED DESCRIPTION OF THE INVENTION

Embodiments of the invention will now be described by way of example with reference to the accompanying drawings, of which:

BRIEF DESCRIPTION OF THE DRAWINGS

Referring to FIG. 1, the phase diagram shows the effect of addition of isopropyl myristate, to mixtures of propylene glycol and a co-solvent (Transcutol). The phase boundary is represented by the curve joining the points of the single-phase system where the polar lipid is at unit, saturated thermodynamic activity. The area to the left of the phase boundary relates to single-phase systems and, as can be seen on following the phase boundary curve from 70:30 glycol:Transcutol to 10:90 glycol:Transcutol, the polar lipid concentration can be increased while saturation is maintained. For each ratio of glycol and Transcutol, a plotted point represents the maximum amount of isopropyl myristate that the system can tolerate whilst still remaining single phase.

The different carrier systems which from the phase diagram are seen to be possible in terms of enabling inclusion of the polar lipid at saturation amounts have different solubilising powers for diclofenac.

Figure 2:
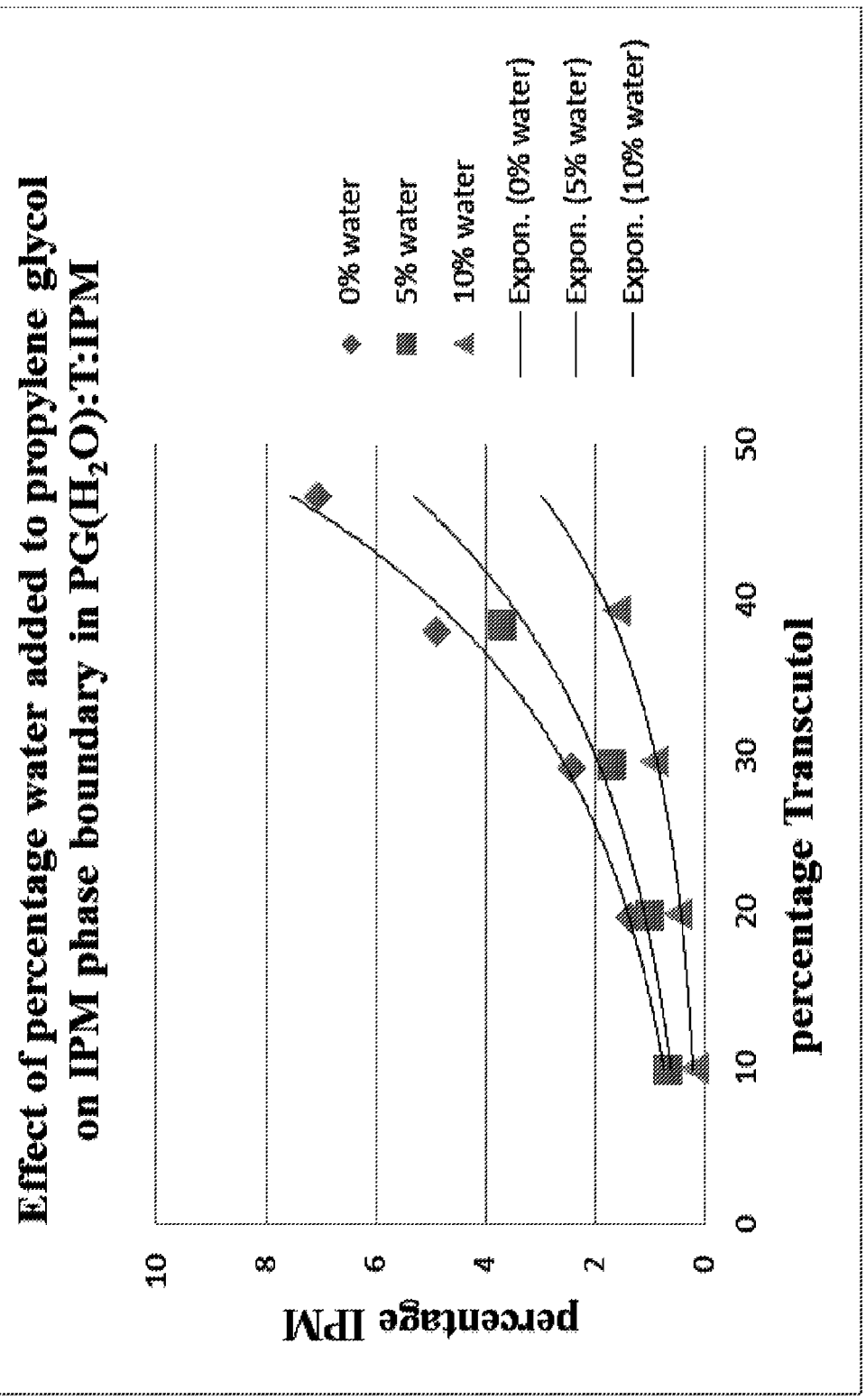
FIG. 2 is a graph showing the effect on the phase boundary of FIG. 1 of addition of water.

Referring to FIG. 2, it can be seen how the presence of water at 5% and 10% based on propylene glycol reduces the amount of isopropyl myristate which can be tolerated for a single-phase system.

In terms of the concentration of diclofenac in the composition, it is desirable to provide a dose level sufficient to sustain the percutaneous absorption process and to achieve therapeutic tissue levels at the target site resulting in inhibitory concentrations in the range $IC_{90-99}$. Taking account of steady state plasma levels, diclofenac clearance rates and the area over which a topical formulation is typically applied, compositions according to the present invention can be formulated to provide a target in vivo flux of between 5 and 25, preferably 10-20, µg/cm$^2$/hr which, assuming a twice daily (12 hours) dosing regime, requires a concentration of diclofenac of around 2.5% by weight, within a broader range of from 0.5 to 5% by weight. Alternatively, the diclofenac may be in a range of 0.5 to 2.5%, such as 0.5 to 1.5%, by weight relative to the total weight of the composition.

Figure 1:
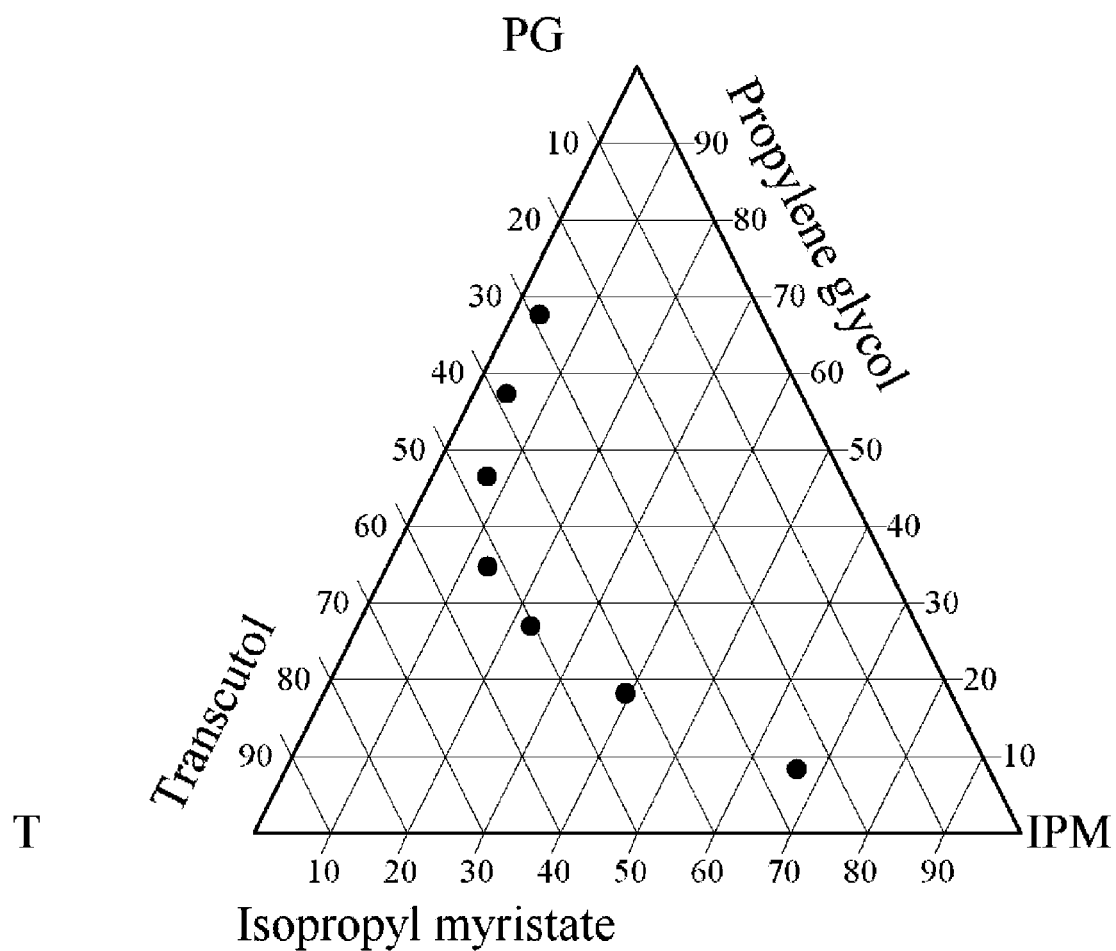
FIG. 1 is a phase diagram for comparative purposes of a carrier system comprising propylene glycol (PG), Transcutol (T) and isopropyl myristate (IPM), but no added water.

Overall, to provide a saturation level of diclofenac in the range of approximately 0.5% to 5.0% concentration by weight, and to optimize the glycol and polar lipid component, it is preferred to employ carrier systems on or close to the phase boundary and relatively rich in glycol, that is, those systems which lie in the upper part of the phase diagram of FIG. 1.

In order to predict in vivo rates of human skin penetration, in vitro experiments are generally used, since there is an established correlation between in vitro and in vivo performance. Systems such as shown in FIG. 1 have been found to provide optimised levels of flux across human skin, and very significant enhancement of flux compared with Voltarol Emulgel as control.

In the examples described below, all ingredients comply with the requirements and standards of the US Pharmacopeia (USP), which also applies as appropriate elsewhere throughout this specification and claims.

EXAMPLE 1

By way of example, diclofenac formulations are shown below. The numbers in parentheses are the percentage by weight of the carrier system ingredients relative to the total weight of the carrier system ingredients rather than relative to the composition as a whole.

TABLE 1

|  | 1 | 2 | 3 | 4 |
|---|---|---|---|---|
| Diclofenac acid | 1 | 2 | 4 | 5 |
| Propylene glycol | 42.79 (61.15%) | 42.79 (61.15%) | 42.79 (61.15%) | 42.79 (61.15%) |
| Transcutol P | 19.72 (28.18%) | 19.72 (28.18%) | 19.72 (28.18%) | 19.72 (28.18%) |
| Isopropyl myristate | 2.47 (3.53%) | 2.47 (3.53%) | 2.47 (3.53%) | 2.47 (3.53%) |
| Dimethicone (Silicone fluid 0.65 CST) | 1.5 | 1.5 | 1.5 | 1.5 |
| HPC HF | 2 | 2 | 2 | 2 |
| Water | 5 (7.14%) | 5 (7.14%) | 5 (7.14%) | 5 (7.14%) |
| Volatile pH adjuster |  | As required to give pH 7 |  |  |
| IPA (to 100) | 25.52 | 24.52 | 22.52 | 21.52 |
| Total | 100 | 100 | 100 | 100 |

Further compositions according to the invention are set out in Tables 2 and 3 below. In Table 2, the compositions are based on a solution of polyethylene glycol with 10% water ("PG10") and in Table 3 the compositions are based on a solution of polyethylene glycol with 5% water ("PG5"). The solutions are mixed with transcutol in different ratios to form stock solutions and isopropyl myristate added dropwise until a second, non-miscible, phase becomes apparent; the phase boundary is recorded as the composition of the immediately previous drop(s). Compositions were prepared at 20° C. Amounts are in percentages by weight, calculated from actual weights used.

TABLE 2

| Stock ratio | 80:20 | 70:30 | 60:40 |
|---|---|---|---|
| "PG10" | 79.61 | 69.35 | 59.04 |
| Propylene glycol (from "PG10") | 71.65 | 62.41 | 53.14 |
| Water (from "PG10") | 7.96 | 6.94 | 5.90 |
| Transcutol | 19.9 | 27.72 | 39.36 |
| Isopropyl myristate | 0.49 | 0.93 | 1.60 |

TABLE 3

| Stock ratio | 90:10 | 80:20 | 70:30 | 60:40 |
|---|---|---|---|---|
| "PG5" | 89.34 | 79.19 | 66.82 | 57.79 |
| Propylene glycol (from "PG5") | 80.46 | 71.27 | 61.94 | 52.01 |
| Water (from "PG5") | 8.94 | 7.92 | 6.88 | 5.78 |
| Transcutol | 9.93 | 19.80 | 29.50 | 38.52 |
| Isopropyl myristate | 0.67 | 1.01 | 1.68 | 3.69 |

TABLE 4

| | Whole formulations based on 80:20 residual phase from Table 3 | | | |
|---|---|---|---|---|
| Ingredients | 1.00% diclofenac acid (% w/w) | 1.86% diclofenac acid (% w/w) | 2.00% diclofenac acid (% w/w) | 2.00% diclofenac acid (% w/w) |
| Diclofenac acid | 1.00 | 1.86 | 2.00 | 2.00 |
| Propylene glycol | 49.89 (71.27%) | 49.89 (71.27%) | 49.89 (71.27%) | 35.64 (71.27%) |
| Transcutol P | 13.86 (19.80%) | 13.86 (19.80%) | 13.86 (19.80%) | 9.90 (19.80%) |

TABLE 4-continued

Whole formulations based on 80:20 residual phase from Table 3

| Ingredients | 1.00% diclofenac acid (% w/w) | 1.86% diclofenac acid (% w/w) | 2.00% diclofenac acid (% w/w) | 2.00% diclofenac acid (% w/w) |
|---|---|---|---|---|
| Isopropyl myristate | 0.71 (1.01%) | 0.71 (1.01%) | 0.71 (1.01%) | 0.50 (1.01%) |
| Dimethicone (Silicone fluid 0.65 CST) | 1.50 | 1.50 | 1.50 | 1.50 |
| HPC HF | 2.0 | 2.0 | 2.0 | 2.0 |
| Water | 5.54 (7.92%) | 5.54 (7.92%) | 5.54 (7.92%) | 3.96 (7.92%) |
| volatile pH adjuster (to give pH 7) | 0.10 | 0.20 | 0.20 | 0.20 |
| IPA to 100 | 25.40 | 24.44 | 24.30 | 44.30 |
| Total | 100.00 | 100.00 | 100.00 | 100.00 |

TABLE 5

Whole formulations based on 70:30 residual phase from Table 3

| Ingredients | 1.00% diclofenac acid (% w/w) | 1.86% diclofenac acid (% w/w) | 2.00% diclofenac acid (% w/w) | 2.00% diclofenac acid (% w/w) |
|---|---|---|---|---|
| Diclofenac acid | 1.00 | 1.86 | 2.00 | 2.00 |
| Propylene glycol | 43.36 (61.94%) | 43.36 (61.94%) | 43.36 (61.94%) | 30.97 (61.94%) |
| Transcutol P | 20.65 (29.50%) | 20.65 (29.50%) | 20.65 (29.50%) | 14.75 (29.50%) |
| Isopropyl myristate | 1.18 (1.68%) | 1.18 (1.68%) | 1.18 (1.68%) | 0.84 (1.68%) |
| Dimethicone (Silicone fluid 0.65 CST) | 1.50 | 1.50 | 1.50 | 1.50 |
| HPC HF | 2.0 | 2.0 | 2.0 | 2.0 |
| Water | 4.81 (6.88%) | 4.81 (6.88%) | 4.81 (6.88%) | 3.44 (6.88%) |
| volatile pH adjuster (to give pH 7) | 0.10 | 0.20 | 0.20 | 0.20 |
| IPA to 100 | 25.40 | 24.44 | 24.30 | 44.30 |
| Total | 100.00 | 100.00 | 100.00 | 100.00 |

Compositions according to the invention have been tested to determine the penetration of diclofenac through human skin in vitro. These compositions have been shown to provide increased penetration of diclofenac relative to prior art compositions.

It is believed that compositions according to the present invention yield enhanced results for skin penetration due to the factors of high thermodynamic activity of the diclofenac as a saturated or supersaturated solution, resulting in increased flux; the ability of the glycol to increase the solubility of the diclofenac acid and the polar lipid in the stratum corneum; and the effect of the polar lipid within the stratum corneum, of increasing diffusivity of diclofenac acid. Since each of these factors is independent of the others, any increase in one of them has a multiplicable effect on the remainder.

The invention claimed is:

1. A topical composition comprising a solution or suspension of an NSAID as active ingredient in a residual carrier system comprising a polyhydric alcohol, a glycol ether, an ester of a higher fatty acid and water, the ingredients of the residual carrier system having the following concentrations in percentages by weight:

| | |
|---|---|
| polyhydric alcohol | 50-90% |
| glycol ether | 7.5-40% |
| ester | 0.5-5% |
| water | up to 10% | in which either the composition or the residual carrier system is in a single phase under ambient conditions.

2. The topical composition according to claim 1, in which the composition is a single phase under ambient conditions.

3. The topical composition according to claim 1, comprising between 2.5% and 10% water by weight.

4. The topical composition according to claim 3, comprising between 5% and 10% water by weight.

5. The topical composition according to claim 1, in which the NSAID as the active ingredient is selected from diclofenac, ketorolac, ketoprofen, naproxen, celecoxib, or a salt thereof.

6. The topical composition according to claim 5, in which the NSAID is diclofenac acid.

7. The topical composition according to claim 1, in which the polyhydric alcohol of the carrier system comprises a glycol.

8. The topical composition according to claim 7, in which the glycol is propylene glycol.

9. The topical composition according to claim 1, in which the ester comprises a polar lipid.

10. The topical composition according to claim 9, in which the polar lipid comprises a branched-chain alkyl ester of a $C_{10}$ to $C_{20}$ saturated carboxylic acid.

11. The topical composition according to claim 10, in which the polar lipid comprises isopropyl myristate.

12. The topical composition according to claim 1, in which the glycol ether comprises a diethylene glycol ether.

13. The topical composition according to claim 12, in which the diethylene glycol ether is diethylene glycol monoethyl ether.

14. The topical composition according to claim 1, in which the carrier system comprises a glycol, a glycol ether, a branched-chain alkyl ester of a $C_{10}$ to $C_{20}$ saturated carboxylic acid and water.

15. The topical composition according to claim 1, in which the amount of the NSAID is between 0.5% and 10% by weight with respect to the total formulation.

16. The topical composition according to claim 1, in which the amount of the NSAID is between 0.5% and 6% by weight with respect to the total formulation.

17. The topical composition according to claim 1, also including a volatile solvent.

18. The topical composition according to claim 17, in which the volatile solvent comprises a lower alcohol containing up to 5 carbon atoms or a liquid-phase ketone.

19. The topical composition according to claim 18, in which the volatile solvent comprises ethanol or isopropyl alcohol.

20. The topical composition according to claim 18, in which the solvent is present in the range 15% to 50% by weight with respect to the total formulation.

21. The topical composition according to claim 1, further comprising a polyhydric alcohol including three or more hydroxyl groups.

22. The topical composition according to claim 21, wherein the polyhydric alcohol including three or more hydroxyl groups is glycerol or sorbitol.

23. The topical composition according to claim 1, wherein the composition comprises a neutralising agent.

24. The topical composition according claim 23, wherein the neutralising agent is volatile.

25. The topical composition according to claim 23, wherein the neutralising agent is liquid ammonia.

26. The topical composition according to claim 1, wherein the composition, before application, has a pH of 6 to 8.

27. The topical composition according to claim 1, wherein the composition, after application, has a pH of 5 or less.

28. The topical composition according to claim 1, wherein the ingredients of the residual carrier system have the following concentrations in percentages by weight:

| | |
|---|---|
| polyhydric alcohol | 50-70% |
| glycol ether | 25-35% |
| ester | 2.5-5% |
| water | 5-10%. |

29. The topical composition according to claim 1, wherein in terms of the total composition, the composition comprises the following ingredients in percentages by weight:

| | |
|---|---|
| polyhydric alcohol | 20-60% |
| glycol ether | 5-30% |
| ester | 0.3-3% |
| water | 2.5-10% |
| lower alcohol | 20-50%. |

30. The topical composition according to claim 1, wherein in terms of the total composition, the composition comprises the following ingredients in percentages by weight:

| | |
|---|---|
| NSAID | 0.5-5% |
| polyhydric alcohol | 25-50% |
| glycol ether | 10-25% |
| ester | 1-2.5% |
| water | 2.5-10% |
| lower alcohol | 20-50%. |

31. A topical composition for application of an NSAID, the composition comprising a solution or suspension of the NSAID as active ingredient in a carrier system comprising a polyhydric alcohol, a glycol ether, an ester of a higher fatty acid and water, wherein the composition is in a single phase at ambient conditions and the ingredients thereof have the following concentrations in percentages by weight relative to the total composition:

| | |
|---|---|
| polyhydric alcohol | 20-60% |
| glycol ether | 5-30% |
| ester | 0.3-3% |
| water | 2.5-10% |
| lower alcohol | 20-50%. |

32. The topical composition according to claim 31, wherein the composition comprises the following ingredients in percentages by weight:

| | |
|---|---|
| NSAID | 0.5-5% |
| polyhydric alcohol | 25-50% |
| glycol ether | 10-25% |
| ester | 1-2.5% |
| water | 2.5-10% |
| lower alcohol | 20-50%. |

33. The method of treating inflammation in a subject in need thereof, comprising topically administering the topical composition of claim 1 to the subject.

* * * * *